(12) United States Patent
Mukasa et al.

(10) Patent No.: US 6,977,053 B2
(45) Date of Patent: Dec. 20, 2005

(54) MANUFACTURING METHOD OF FRONT-END COMPONENT OF ENDOSCOPE

(75) Inventors: Katsunori Mukasa, Saitama (JP); Hiroaki Fujita, Saitama (JP)

(73) Assignee: Fujinon Corporation, Saitama (JP)

( * ) Notice: Subject to any disclaimer, the term of this patent is extended or adjusted under 35 U.S.C. 154(b) by 399 days.

(21) Appl. No.: 10/246,488

(22) Filed: Sep. 17, 2002

(65) Prior Publication Data

US 2003/0056540 A1    Mar. 27, 2003

(30) Foreign Application Priority Data

Sep. 27, 2001    (JP)    ............................. 2001-297485

(51) Int. Cl.[7] ............................................. B29D 11/00
(52) U.S. Cl. ........................... 264/1.7; 65/39; 65/59.4; 264/2.7
(58) Field of Search .................. 264/1.1, 1.7, 1.33, 264/2.7; 65/39, 59.1, 59.4; 425/808

(56) References Cited

U.S. PATENT DOCUMENTS 4,988,375 A * 1/1991 Bornhauser ................. 65/59.4

FOREIGN PATENT DOCUMENTS

| JP | 10-29825 | * | 2/1998 |
| JP | 10-170794 | | 6/1998 |
| JP | 10-234652 | | 9/1998 |

* cited by examiner

*Primary Examiner*—Mathieu D. Vargot
(74) *Attorney, Agent, or Firm*—Jordan and Hamburg LLP

(57) ABSTRACT

The invention relates to a method of manufacturing a front-end optical component of an endoscope realizing resistance to humidity. In the method of manufacturing a front-end optical component in which a lens is mounted on the front end of a metallic lens-barrel provided on the front end of the inserting portion of an endoscope, the configuration is made such that a lens raw material is placed on the front-end side in the lens-barrel, the lens raw material is press-formed in a heat-softened state with a pair of upper and lower shaping dies, thereby tightly joining the outer edge of the pressed lens raw material to the inner peripheral surface of the lens-barrel.

12 Claims, 4 Drawing Sheets

MANUFACTURING METHOD OF FRONT-END COMPONENT OF ENDOSCOPE

BACKGROUND OF THE INVENTION

1. Field of the Invention

The invention relates to a method of manufacturing a front-end optical component in which a lens is mounted on the front end of the lens-barrel provided at the front-end of the inserting portion of an endoscope.

2. Description of the Related Art

Although a front-end optical component configuring the inserting portion of an endoscope has a lens mounted at the front end of the lens-barrel, the lens is bonded and fixed to the inside surface of the lens-barrel with a epoxy-based adhesive. For example, in the front-end optical components of the endoscopes disclosed in the gazettes of Japanese Patent Laid-Open No. 10-234652 and Japanese Patent Laid-Open No. 10-170794, both of the lens are fixed to the lens-barrels with adhesives.

The main body of the front-end portion in the inserting portion of an endoscope is provided with observing means having an objective optical system positioned in the proximity of illuminating means. The objective optical system is usually configured by a plurality of lenses, and these lenses are mounted in a lens-barrel. Herein, a first lens located on the nearest side to a body to be observed of the lens-barrel is a planoconcave lens, of which concave surface is adapted to be located within the lens-barrel. For example, during testing, a pollution substance, such as a body fluid, can adhere to the surface of the first lens exposed to the outside at the front end of the inserting portion, and the adherence of the pollution substance may impair the visual field of observation. Therefore, the inserting portion is provided with a lens surface-cleaning mechanism for washing out pollution substances from the surface of the first lens. The lens surface-cleaning mechanism is provided with a nozzle for issuing a jet of cleaning fluid toward the outside surface of the first lens, and issues a jet of cleaning fluid, usually washing water, from this nozzle to wash out pollution substances. Then, the mechanism blows pressurized air on the lens surface to remove washing water remaining on the lens surface. Further, when existing in a body cavity, the first lens is in a state of about the same temperature as the body temperature. In the case of an electronic endoscope, the first lens can be in a state of a higher temperature than the body temperature due to the existence of a heating element, such as a solid image sensor. On the other hand, the washing water is not particularly heated up, and therefore the temperature of the washing water is held about at the same temperature as the room temperature. For this reason, when the washing water is jetted on the outside surface of the first lens, the first lens can be quickly cooled. As a result of cooling the first lens, if moisture is contained in the air in the lens-barrel, fogging or condensation can be caused on the inside surface side of the first lens. Moreover, because the inside surface of the first lens is configured by a concavely curved surface and its curvature is large, the temperature decrease is most remarkable at the central portion thinnest in thickness and its neighborhood in the first lens, thus resulting in fogging or condensation concentrated on the central portion in the concave surface of the first lens. Since light beams necessary for image formation is concentrated in the central portion of the concave surface of the first lens, least fogging of this region would cause rapid decrease in the image quality of observational images obtained, thereby resulting in a very difficult-to-look image. Further, in some other cases, when the front end of the inserting portion is also quickly cooled, there is also a fear that fogging or condensation may take place on the first lens and the like.

In this manner, since fogging or condensation can possibly take place on the lens (first lens) of the front-end optical component of an endoscope, as a measure for preventing this, no moisture-containing gas such as dry air and nitrogen gas has been filled in the space in the lens-barrel.

In the first place, taking in moisture into the lens-barrel is caused by that the first lens is bonded to the lens-barrel with an adhesive and moisture can pass through this adhesive. The adhesive is pervious to water in nature, and therefore moisture enters into the lens-barrel through an adhesive layer between the first lens and the lens-barrel, resulting in fogging of the first lens.

SUMMARY OF THE INVENTION

Therefore, the invention has an object to provide a method of manufacturing a front-end optical component able to prevent the entry of moisture into a lens-barrel, in which a lens is fixed, without using an adhesive, on the front-end side of a lens-barrel configuring the front-end optical component of an endoscope.

In order to achieves the above object, in a method of manufacturing a front-end optical component in which a lens is mounted on the front end of a metallic lens-barrel provided on the front end of the inserting portion of an endoscope, the invention configures the front-end optical component in such a manner that a lens raw material is placed on the front-end side in the lens-barrel, the lens raw material is press-formed in a heat-softened state with a pair of upper and lower shaping dies, thereby tightly joining the outer edge of the pressed lens raw material to the inner peripheral surface of the lens-barrel.

According to the invention, a lens raw material is placed on the front-end side in the lens-barrel, the lens raw material is press-formed in a heat-softened state with a pair of upper and lower shaping dies, thereby tightly joining the outer edge of the pressed lens raw material to the inner peripheral surface of the lens-barrel, and further, the coefficient of linear thermal expansion of a metallic material configuring the lens-barrel is selected to be equal to or more than the coefficient of linear thermal expansion of the lens raw material such that the lens-barrel can fasten the lens raw material in a cooling process after heat pressurizing. Thereby, the lens raw material and the front end side of the lens-barrel can be joined to each other into one piece without using of an adhesive as in a conventional method. Because of no use of an adhesive, there is no fear of the intrusion of humidity into the lens barrel through the adhesive layer.

DETAILED DESCRIPTION OF THE PREFERRED EMBODIMENTS

Figure 1:
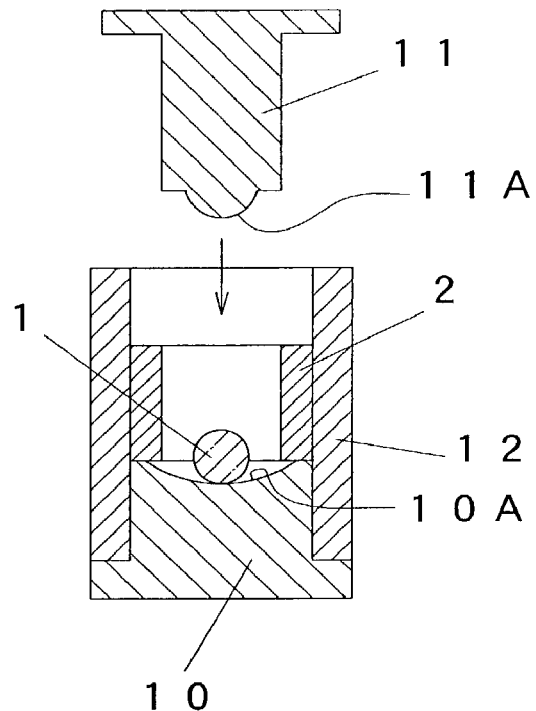
FIG. 1 is a cross sectional view for showing a manufacturing process for a front-end optical component according to the invention.

In FIG. 1, a transfer surface 10A is shape on the top surface of a lower die 10, a transfer surface 11A is shaped on the bottom surface of a upper die 11, and a lens raw material 1 is adapted to be press-formed by a pair of the upper and lower shaping dies 10 and 11. A guide die 12 is mounted on the lower die 10, and the barrel die 12 and the lower die 10 together supports a metallic lens-barrel 2. The upper die 11 is adapted to be inserted into the lens-barrel 2. Further, the lens raw material 1 is placed on the transfer surface 10A of the lower die 10, and positioned on the front-end side of the lens-barrel 2. The front end of the lens-barrel 2 is placed on the lower die 10 to straddle the outer periphery of the transfer surface 10A.

Figure 2:
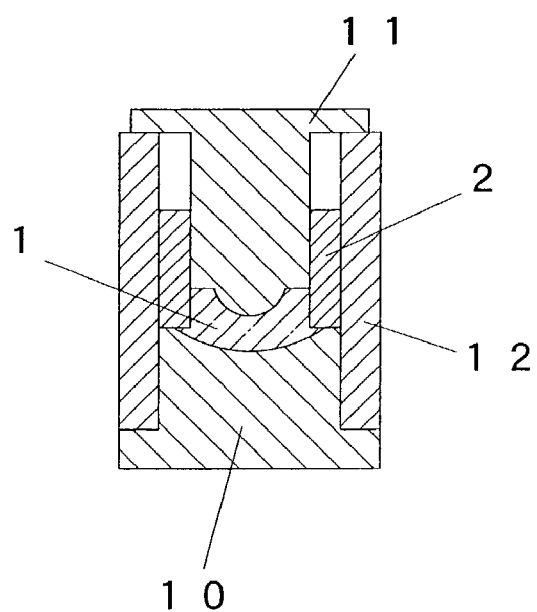
FIG. 2 shows a cross sectional view in press forming.

FIG. 2 is a cross sectional view for showing a state in which the upper die 11 is inserted into the lens-barrel 2 to press the lens raw material 1 in cooperation with the lower die 10. Herein, the outer edge of the pressed lens raw material 1 is tightly joined to the inner peripheral surface of the front-end side of the lens-barrel 2.

Figure 3:
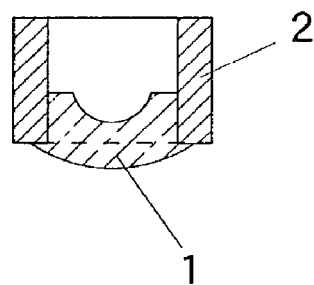
FIG. 3 is a cross sectional view for showing the state of the lens raw material joined to the lens-barrel, which is taken out from the shaping die.
Figure 4:
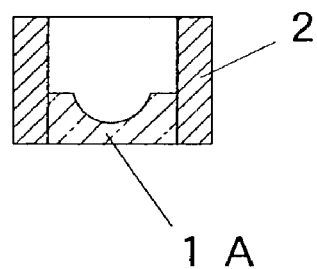
FIG. 4 shows across sectional view of a front-end optical component obtained by polishing the lens raw material.

After the lens raw material 1 is properly cooled down in the pressed state shown in FIG. 2, the shaping dies is opened and then the lens barrel 2 and the lens raw material 1 are taken out. FIG. 3 shows an entity taken out at this time. In FIG. 3, a portion of the lens raw material 1 pressed between the upper and lower dies 10 and 11 is shaped projecting toward the front-end side of the lens barrel 2 from its inside, and this projection-shaped portion is polished and finished into a plane (see FIG. 4). FIG. 4 is a cross sectional view for showing the state of a completed front-end optical component of an endoscope, and the lens raw material 1 is configured into a lens 1A. The lens 1A is a planoconcave lens.

Stainless steel is preferable as a metallic material used for the lens-barrel 2. The stainless steel used in the embodiment was selected to have a coefficient of linear thermal expansion of $125 \times 10^{-7}$ (1° C.) and the coefficient of linear thermal expansion of the lens raw material 1 was selected to be $124 \times 10^{-7}$ (1° C.). Preferably, the material of the lens-barrel 2 has a coefficient of linear thermal expansion equal to or more than that of the lens raw material 1. In a cooling process subsequent to heat pressurizing of the lens raw material 1, in order that the lens-barrel 2 expanded by heating and thereafter shrinking by cooling can fasten the lens raw material, the coefficient of linear thermal expansion of a metallic material configuring the lens-barrel 2 should be equal to or more than that of the lens raw material. SUS 430, SUS 430 F, SUS 444, and SUS 444F or the like can be suitably used as the stainless steel. The coefficients of linear thermal expansion of these stainless steel materials are in the order of 100 to $170 \times 10^{-7}$. When a general optical glass is used as the lens raw material 1, its coefficient of linear thermal expansion is in the order of 70 to $120 \times 10^{-7}$. In the case of using SFS 01 of a lead oxide-based glass among optical glass materials, its coefficient of linear thermal expansion is $100 \times 10^{-7}$. The coefficient of linear thermal expansion of the lens raw material 1 used in the embodiment, SFLD 21 (made in Sumita Optical Glass Corporation) is $124 \times 10^{-7}$. A difference between the coefficients of linear thermal expansion of the lens-barrel 2 and the lens raw material 1 is desirably not less than 0 and not more than 100. If the difference is larger than this value, there is a fear that the lens-barrel may too strongly fasten the lens during cooling.

Figure 5:
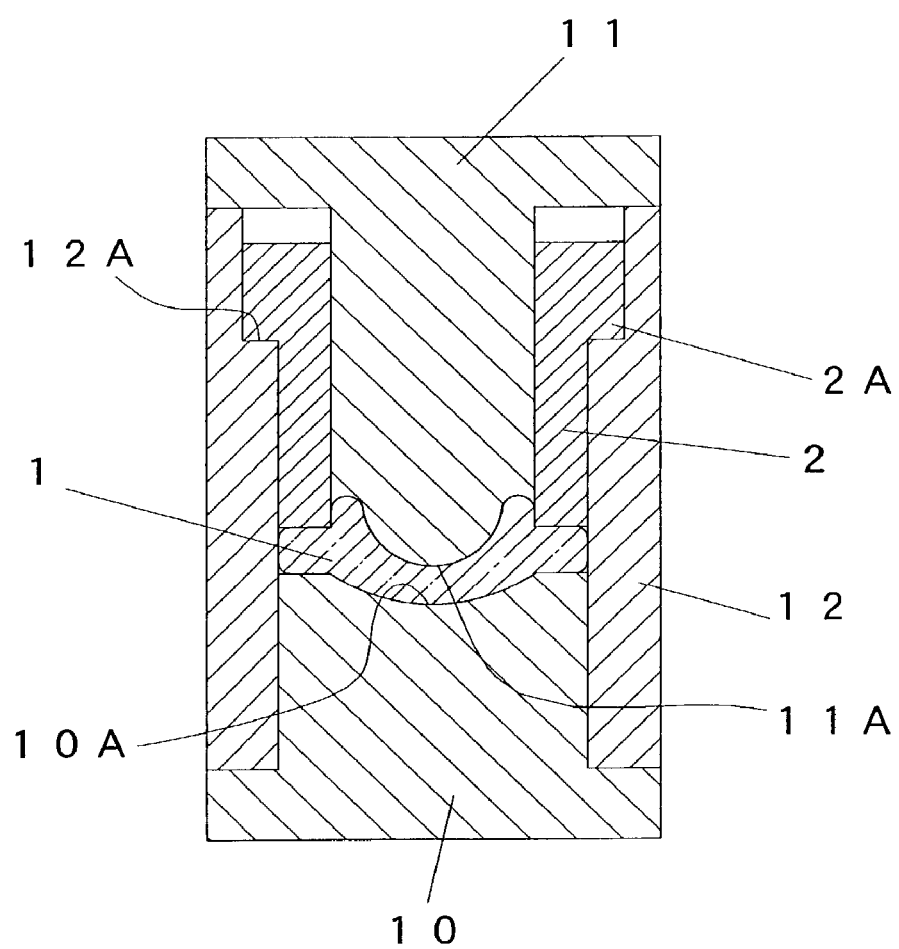
FIG. 5 shows a cross sectional view of a shaping die in press forming, showing another embodiment.
Figure 6:
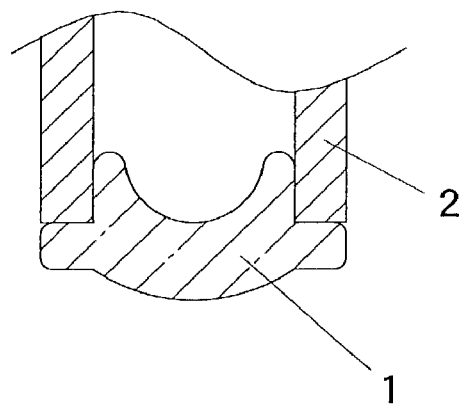
FIG. 6 is a cross sectional view of an entity taking out from the shaping die as shown in FIG. 5.
Figure 7:
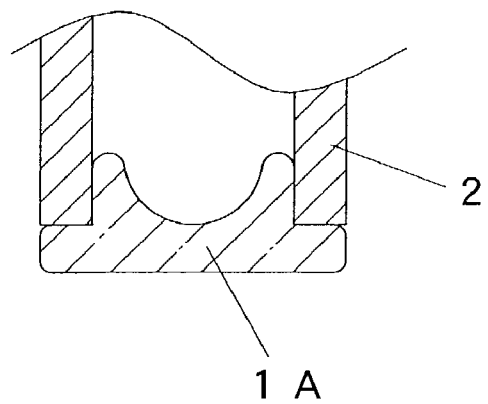
FIG. 7 is a cross sectional view for showing a front-end optical component obtained by polishing the lens raw material.

FIG. 5 is a cross sectional view of a shaping die for showing another embodiment. Herein, a guide die 12 is mounted on a lower die 10 having a transfer surface 10A shaped on the top surface thereof, a step portion 12A is shaped on the inner peripheral surface of this barrel die 12. A flange portion 2A shaped on the outer peripheral surface of the lens-barrel 2 is engaged with the step portion 12A such that the lens-barrel 2 may be supported by the barrel die 12, thereby providing a space between the front end of the lens-barrel 2 and the lower die 10. The lens raw material 1 is placed on the transfer surface 10A of the lower die 10, and then a upper die 11 having a transfer surface 11A shaped on the bottom surface thereof is inserted into the lens-barrel 2, thereby press-forming the lens raw material 1. Then, a portion of the press-formed lens material 1 is adapted to be shaped projecting toward the front-end side of the lens-barrel 2 from its inside so as to cover the front end of the lens-barrel 2. FIG. 6 shows an entity taken out from the shaping dies after cooling the lens raw material. In FIG. 6, the front-end surface of the lens-barrel 2 is covered with the lens raw material 1. This lens raw material is polished and finished in a plane in the same manner as described previously (see FIG. 7). As shown in FIG. 7, the outside periphery side of the lens 1A covers the front end of the lens-barrel 2. This is because an electric current-passing tool may be included in treatment tools sent out from a treatment tool-inserting channel of the inserting portion adjacent to the front-end optical component of an endoscope, and such a tool may make contact with the front end of the metallic lens-barrel 2, thus having an adverse effect on the front-end optical component by energizing it. Thus, the front end of the lens-barrel 2 is covered with the outer edge of the lens 1A, and thus the treatment tool makes contact with the outer edge of the lens 1A covering the front end of the lens-barrel 2 but it does not touch on the lens-barrel 2, thus eliminating a fear of energization of the lens-barrel 2.

What is claimed is:

1. A method of manufacturing a front-end optical component in which a lens is mounted on the front end of a metallic lens-barrel provided on the front end of the inserting portion of an endoscope, comprising the steps of:

placing a lens raw material on the front-end side in the lens-barrel, press-forming the lens raw material in a heat-softened state with a pair of upper and lower shaping dies, tightly joining the outer edge of the pressed lens raw material to the inner peripheral surface of the lens-barrel; and wherein the front end of the lens-barrel is placed so as to straddle an outer periphery of a transfer surface shaped on a top surface of the lower die of said pair of upper and lower shaping dies, a guide die is provided so as to enclose the periphery of the lens-barrel, the upper die has a transfer surface shaped on a bottom surface thereof and is provided in the lens-barrel so as to able to be inserted in and withdrawn from it, a portion of the lens raw material press-formed by the upper and lower dies is formed projecting toward the front-end side of the lens-barrel from its inside, and the projection-shaped portion is polished and finished.

2. The method of manufacturing a front-end optical component of an endoscope according to claim 1, wherein a coefficient of linear thermal expansion of a metallic material configuring said lens-barrel is selected to be equal to or more than the coefficient of linear thermal expansion of the lens raw material such that the lens-barrel can fasten the lens raw material in a cooling process after heat pressurizing.

3. The method of manufacturing a front-end optical component of an endoscope according to claim 1, wherein the coefficient of linear thermal expansion of a metallic material configuring the lens-barrel is 100 to 170, and the coefficient of linear thermal expansion of the lens raw material is 70 to 160.

4. The method of manufacturing a front-end optical component of an endoscope according to claim 3 wherein a difference between the coefficients of linear thermal expansion of the lens-barrel and the lens raw material is not more than 100 at most.

5. The method of manufacturing a front-end optical component of an endoscope according to claim 2, wherein the coefficient of linear thermal expansion of a metallic material configuring the lens-barrel is 100 to 170, and the coefficient of linear thermal expansion of the lens raw material is 70 to 160.

6. The method of manufacturing a front-end optical component of an endoscope according to claim 5 wherein a difference between the coefficients of linear thermal expansion of the lens-barrel and the lens raw material is not more than 100 at most.

7. A method of manufacturing a front-end optical component in which a lens is mounted on the front end of a metallic lens-barrel provided on the front end of the inserting portion of an endoscope, comprising the steps of:
   placing a lens raw material on a front-end side in a lens-barrel,
   press-forming lens raw material in a heat-softened state with a pair of upper and lower shaping dies, and
   tightly joining the outer edge of the pressed lens raw material to an inner peripheral surface of the lens-barrel; and
   wherein a guide die is mounted on the lower die having a transfer surface shaped on a top surface thereof, a step portion is shaped on an inner peripheral surface of the guide die, a flange portion shaped on an outer peripheral surface of the lens-barrel is engaged with the step such that the lens-barrel may be supported by the guide die, thereby shaping space between the front end of the lens-barrel and the lower die, the lens raw material is placed on the transfer surface of the lower die, the upper die having a transfer surface shaped on the bottom surface thereof is inserted into the lens-barrel to press-form the lens raw material, a portion of the press-formed lens raw material is formed projecting toward the front-end side of the lens barrel from its inside so as to cover the front end of the lens-barrel, and the projection-shaped portion is polished and finished except for the covered front end portion of the lens-barrel.

8. The method of manufacturing a front-end optical component of an endo scope according to claim 7, wherein a coefficient of linear thermal expansion of a metallic material configuring said lens-barrel is selected to be equal to or more than a coefficient of linear thermal expansion of the lens raw material such that the lens-barrel can fasten the lens raw material in a cooling process after heat pressurizing.

9. The method of manufacturing a front-end optical component of an endoscope according to claim 7 wherein a coefficient of linear thermal expansion of a metallic material configuring the lens-barrel is 100 to 170, and a coefficient of linear thermal expansion of the lens raw material is 70 to 160.

10. The method of manufacturing a front-end optical component of an endoscope according to claim 9, wherein a difference between the coefficients of linear thermal expansion of the lens-barrel and the lens raw material is not more than 100 at most.

11. The method of manufacturing a front-end optical component of an endoscope according to claim 8 wherein the coefficient of linear thermal expansion of a metallic material configuring the lens-barrel is 100 to 170, and the coefficient of linear thermal expansion of the lens raw material is 70 to 160.

12. The method of manufacturing a front-end optical component of an endoscope according to claim 11 wherein a difference between the coefficients of linear thermal expansion of the lens-barrel and the lens raw material is not more than 100 at most.

* * * * *